(12) United States Patent
Nambu et al.

(10) Patent No.: US 7,792,239 B2
(45) Date of Patent: Sep. 7, 2010

(54) RADIATION DETECTOR AND X-RAY CT APPARATUS

(75) Inventors: Shuya Nambu, Nasushiobara (JP); Hiroaki Miyazaki, Otawara (JP); Minoru Horinouchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 121 days.

(21) Appl. No.: 12/034,946

(22) Filed: Feb. 21, 2008

(65) Prior Publication Data

US 2008/0205586 A1 Aug. 28, 2008

(30) Foreign Application Priority Data

Feb. 28, 2007 (JP) .............................. 2007-050245

(51) Int. Cl.
*A61B 6/00* (2006.01)
(52) U.S. Cl. ............................................ 378/4; 378/19
(58) Field of Classification Search .................... 378/4, 378/19, 98.8; 250/370.09, 370.11
See application file for complete search history.

(56) References Cited

U.S. PATENT DOCUMENTS 6,139,337 A * 10/2000 Englert et al. ................. 439/91

FOREIGN PATENT DOCUMENTS

JP 2005-283441 10/2005

* cited by examiner

*Primary Examiner*—Irakli Kiknadze
(74) *Attorney, Agent, or Firm*—Oblon, Spivak, McClelland, Maier & Neustadt, L.L.P.

(57) ABSTRACT

A radiation detector includes a detector block, cables, connectors, and circuit substrates. The detector block has a plurality of radiation detector modules arranged in a slice direction. The cables extend in the slice direction and configured to receive signals from the radiation detector modules of the detector block. The connectors are associated with the cables, respectively, and are spaced, one from another, in the slice direction. The circuit substrates are configured to receive signals via the connectors from the radiation detector modules of the detector block.

12 Claims, 5 Drawing Sheets

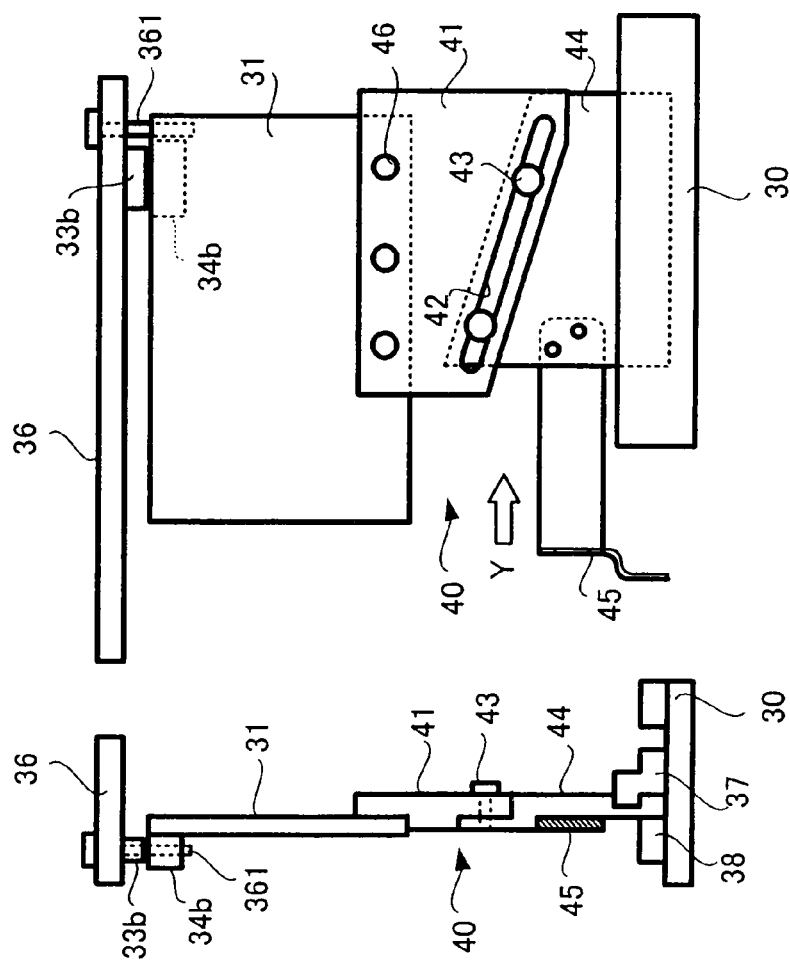

RADIATION DETECTOR AND X-RAY CT APPARATUS

CROSS-REFERENCE TO RELATED APPLICATION

This application is based upon and claims the benefit of priority from the prior Japanese Patent Application No. 2007-50245, filed on Feb. 28, 2007, the entire contents of which are incorporated herein by reference.

BACKGROUND OF THE INVENTION

1. Field of the Invention

The present invention relates to a radiation detector and an X-ray computed tomography (CT) apparatus incorporating the radiation detector.

2. Description of the Related Art

X-ray CT apparatus developed hitherto have an X-ray tube and a radiation detector. X-rays generated in the X-ray tube are applied to an object. After passing through the object, the X rays are applied to the radiation detector.

The radiation detector has a plurality of detector modules that are arranged in a substantially circular arc, in the channel direction that intersects at right angles with the axis of an object. Each detector module has a scintillator array and a photodiode array. The scintillator array converts the incident radiation (i.e., X rays) into a light beam. The photodiode array converts the light beam into an electric signal. The electric signals from the respective detector modules are amplified by an amplifier. The signals amplified are converted to a digital signal by a data acquisition system (DAS) unit.

The electric signals from the respective detector modules are supplied to amplifier substrates through a flexible cable. The amplifier substrates amplify the signals, which are supplied to the DAS unit. The DAS unit converts the signals to a digital signal. A connector connects the flexible cable to the amplifier substrates.

Jpn. Pat. Appln. Laid-Open Publication No. 2005-283441 discloses a radiation detector.

Recently, large radiation detectors have been developed. To provide a large radiation detector, detector modules are arranged, forming two columns that lie side by side along the axis of an object (or in the slice direction). The detector modules constituting each column are arranged in the channel direction.

The radiation detector is held in the gantry of an X-ray CT apparatus. If the detector modules are arranged, forming two columns that lie side by side in the slice direction, the depth of the radiation detector will increase.

Since the detector modules are arranged in the deepest section of the housing, the connectors of the detector modules are difficult to remove from, and insert into, the housing during the manufacture or the maintenance work. Consequently, the connector may not be well connected, or much time may be required to remove and insert the connectors. Particularly, when the number of detector modules and amplifier substrates is large, operability is further deteriorated.

SUMMARY OF THE INVENTION

An object of the present invention is to provide a radiation detector in which the detector modules and the amplifier substrates can be easily connected, thus enhancing the manufacture efficiency and maintenance efficiency, and to provide an X-ray CT apparatus that incorporates the radiation detector.

According to a first aspect of the present invention, there is provided a radiation detector, comprising: a detector block having a plurality of radiation detector modules arranged in a slice direction; a plurality of cables configured to receive signals from the radiation detector modules of the detector block; a plurality of connectors associated with the cables, respectively, and spaced, one from another, in the slice direction; and circuit substrates configured to receive signals via the connectors from the radiation detector modules of the detector block.

According to a second aspect of the present invention, there is provided an X-ray CT apparatus, comprising: an X-ray tube configured to apply an X-ray beam to an object; and a radiation detector opposed to the X-ray tube, shaped like a circular arc and configured to detect X-rays passed through the object and convert the X-rays into an electric signal. The radiation detector includes: a detector block having a plurality of radiation detector modules arranged in a slice direction; a plurality of cables to receive signals from the radiation detector modules of the detector block; a plurality of connectors associated with the cables, respectively, and spaced, one from another, in the slice direction; and circuit substrates configured to receive signals via the connectors from the radiation detector modules of the detector block.

According to a third aspect of the present invention, there is provided an X-ray CT apparatus, comprising: an X-ray tube configured to apply an X-ray beam to an object; a detector block having a plurality of radiation-detecting element arrays and configured to detect X-rays passed through the object; circuit substrates configured to process electric signals from the detector block; first connectors configured to electrically connect the circuit substrates to the detector block; second connectors spaced apart from the first connectors and configured to electrically connect the circuit substrates to the detector block; and coupling mechanisms configured to couple and decouple connectors provided at the detector block and constituting the first connectors to and from the connectors provided at the circuit substrates.

According to a fourth aspect of the present invention, there is provided an X-ray CT apparatus, comprising: an X-ray tube configured to apply an X-ray beam to an object; first detector modules, each including a plurality of radiation-detecting element arrays, and configured to detect X-rays passed through the object; second detector modules, each including a plurality of radiation-detecting element arrays, and arranged beside the first detector modules with respect to a slice direction; circuit substrates configured to process electric signals from the first detector modules and second detector modules; first connectors configured to electrically connect the first detector modules to the circuit substrates; and second connectors configured to electrically connect the second detector modules to the circuit substrates.

BRIEF DESCRIPTION OF THE DRAWINGS

FIG. 6A is a front view explaining how to secure the radiation detector according to the embodiment of the invention; and FIG. 6B and FIG. 6C are side views explaining how to secure the radiation detector according to the embodiment of the invention.

DETAILED DESCRIPTION OF THE PREFERRED EMBODIMENTS

Figure 1:
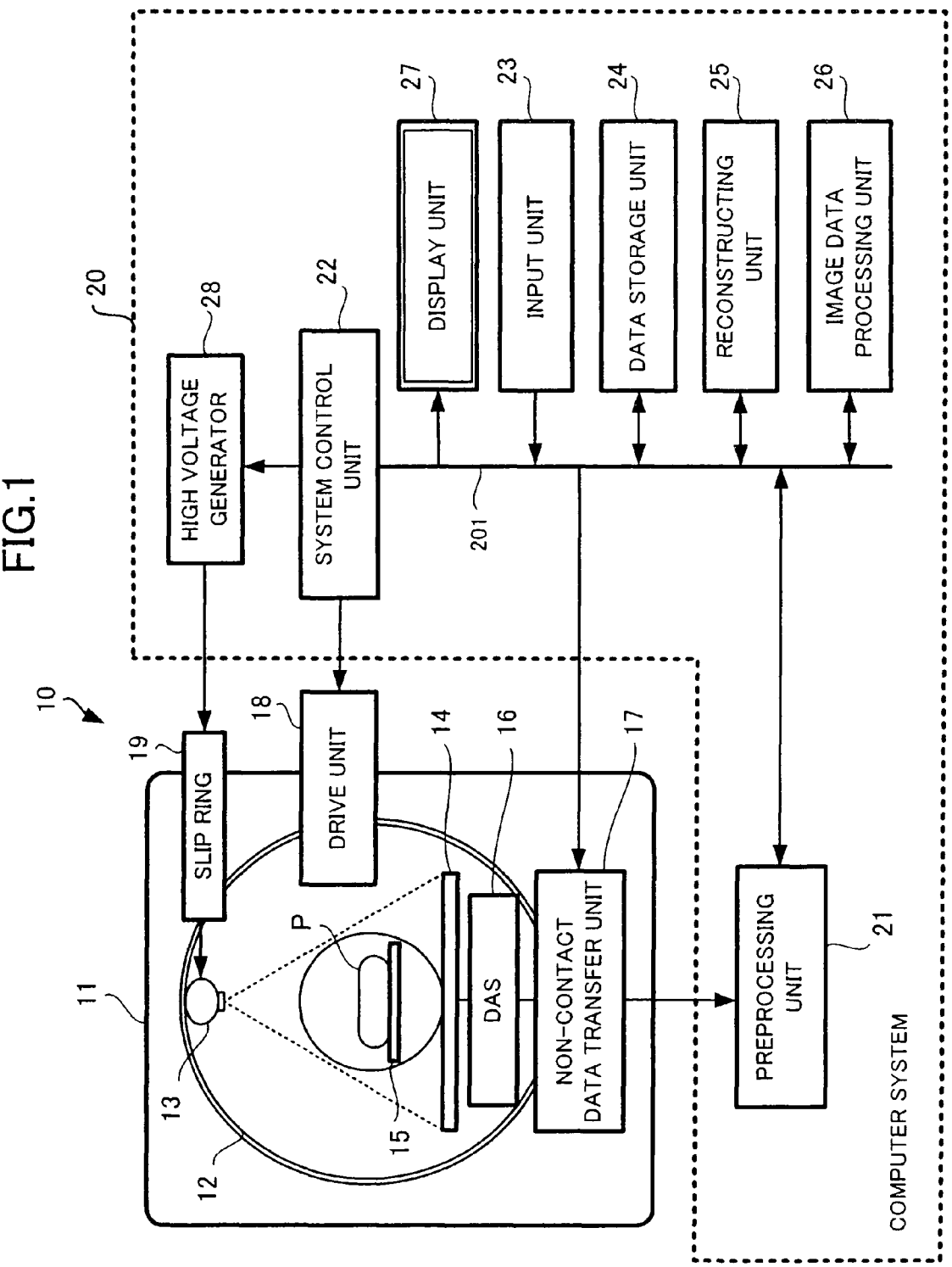
FIG. 1 is a block diagram showing an X-ray CT apparatus according to an embodiment of the present invention.

Throughout this description, the embodiments and examples shown should be considered as exemplars, rather than limitations on the apparatus of the present invention.

An embodiment of the present invention will be described in detail with reference to the accompanying drawings. In each drawing, the components identical to those shown in any other drawing are designated by the same reference numerals.

FIG. 1 shows the overall configuration of an X-ray CT apparatus according to an embodiment of this invention. The X-ray CT apparatus 10 shown in FIG. 1 is designed for use in medical diagnosis. The X-ray CT apparatus 10 has a gantry 11 and a rotating ring 12. The rotating ring 12 is provided in the gantry 11 and can be rotated by a rotation mechanism (not shown). The rotation ring 12 holds an X-ray tube 13. The X-ray tube 13 generates X-rays, which may be applied to an object P lying in an effective visual field region.

A radiation detector 14 is arranged facing the X-ray tube 13. The rotation ring 12 has a center opening. Into the center opening, a tabletop 15 on which the object P lies is inserted. The radiation detector 14 detects the X-rays that have passed through the object P and converts these X-rays into an electric signal. The electric signal is supplied to a data-acquisition system unit 16 (hereinafter referred to as DAS unit). The DAS unit 16 amplifies the signal and converts the same into digital data.

The radiation detector 14 has a plurality of detector modules. Each detector module includes a plurality of detecting-element arrays, i.e., a scintillator array and a photodiode array. The detector modules are arranged in two directions, i.e., channel direction C and slice direction S. Thus, the detector modules are arranged in a matrix form. More precisely, the detector modules are arranged along a circular arc having the center at the focal point of the X-ray tube 13, as will be described later in detail.

The digital data (projection data) from the DAS unit 16 is transmitted to a computer system 20 via a non-contact data transfer unit 17. A drive unit 18 is provided to drive the gantry 11. The gantry 11 has a slip ring 19.

The computer system 20 is incorporated in a console (not shown), and includes a pre-processing unit 21 that receives the projection data coming through the data transfer unit 17. The pre-processing unit 21 performs pre-process, such as data correction, on the projection data. The data pre-processed is output on a bus line 201.

To the bus line 201, there are connected the system control unit 22, an input unit 23, a data storage unit 24, a reconstructing unit 25, an image data processing unit 26, and a display unit 27.

The system control unit 22 functions as host controller. It controls the components of the computer system 20, and the drive unit 18 and the high voltage generator 28. The data storage unit 24 stores data such as a tomography image. The reconstructing unit 25 reconstructs 3D image data from the projection data. The image data processing unit 26 can process the data stored in the data storage unit 24 and the image data generated by the reconstructing unit 25. The display unit 27 displays the image formed by processing the image data.

The input unit 23 has a keyboard, a mouse, and the like. When operated by a user (doctor or operator), the input unit 23 makes various settings for data processing and inputs various information items representing the physical conditions of the object and the method of examining the object.

The high voltage generator 28 supplies power via the slip ring 19 to the X-ray tube 13. More precisely, it supplies power (i.e., tube voltage and tube current) that is required for applying X rays to the object. The X-ray tube 13 generates an X-ray beam that diverges in two directions, i.e., slice direction S parallel to the axial direction of the object P, and channel direction C intersecting at right angles with the slice direction S.

Figure 2:
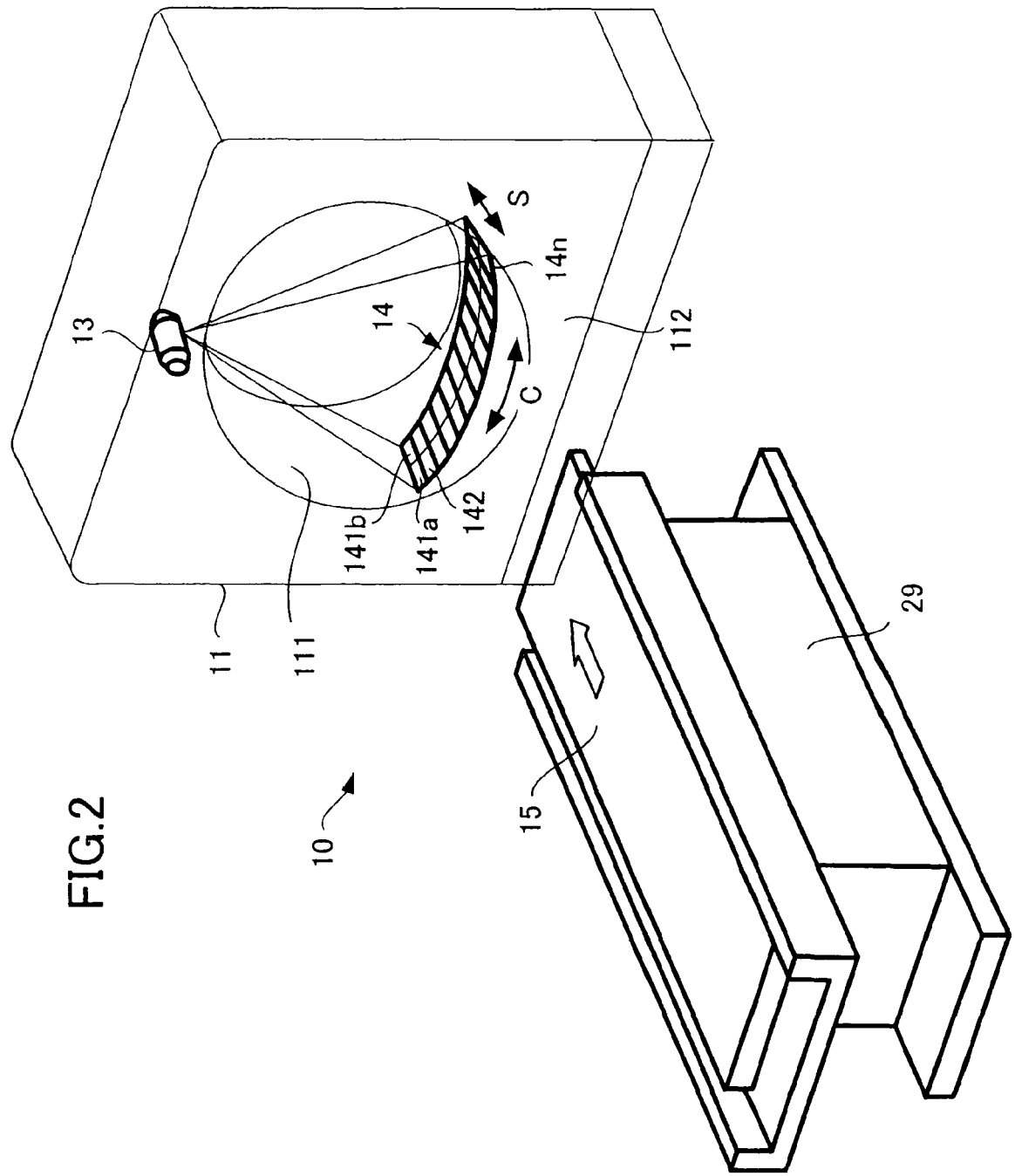
FIG. 2 is a perspective view depicting the X-ray CT apparatus and a radiation detector according to the embodiment of the invention.

FIG. 2 is a diagram representing an outer appearance of the X-ray CT apparatus 10 according to this invention. In FIG. 2, the gantry 11 is indicated by thin lines, and the X-ray tube 13 and radiation detector 14 are indicated by thick lines.

The gantry 11 has an opening 111. The X-ray tube 13 and radiation detector 14 are arranged in the gantry 11, facing each other across the opening 111. The radiation detector 14 includes a plurality of detector modules. The detector modules are arranged in two columns that lie side by side in the slice direction S. The detector modules (n modules) constituting each column are arranged in the channel direction C. The radiation detector 14 is arced as viewed from a front surface 112 of the gantry 11. The tabletop 15 of a bed 29 can be inserted into, and pulled out from, the opening 111 of the gantry 11.

The radiation detector 14 is a multi-column module type that has two module columns arranged, side by side in the slice direction S, each column consisting of n modules arranged in the channel direction C. More specifically, the module column proximal with respect to the front surface 112 consists of detector modules 141a, and the module column distal with respect to the front surface 112 consists of detector modules 141b. Any two modules 141a and 141b adjacent in the slice direction S constitute a detector block.

Figure 3:
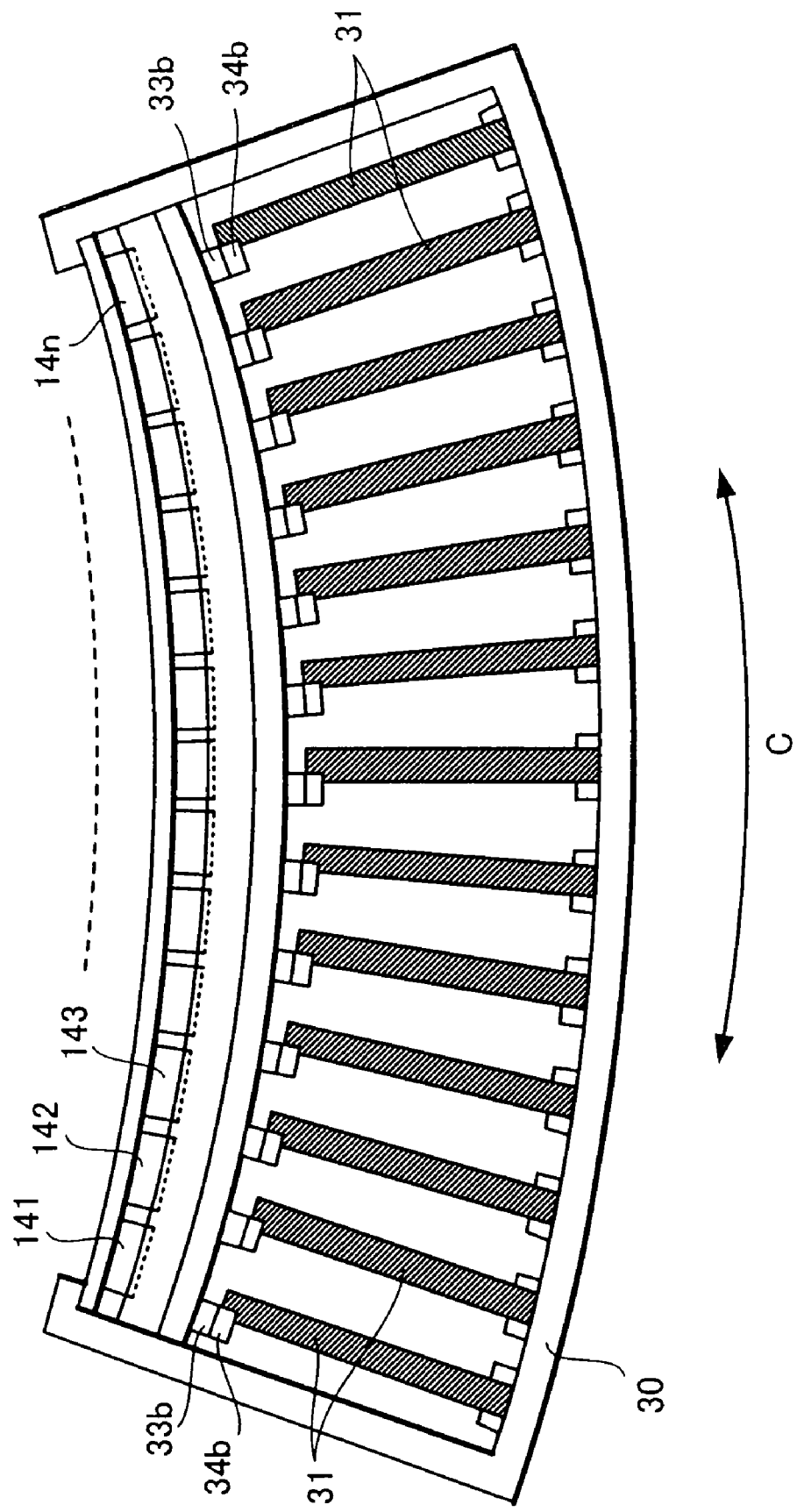
FIG. 3 is a front view of the radiation detector according to the embodiment of the invention, showing an overall configuration thereof.

FIG. 3 shows the overall configuration of the radiation detector 14. As seen from FIG. 3, one amplifier substrate 31 is provided for two detector modules 141a and 141b adjacent in the slice direction S and extends at right angles to the detector modules 141a and 141b. Thus, n amplifier substrates 31 are arranged in the channel direction C.

The detector modules 141 to 14n constituting each column and the amplifier substrates 31 are held in a box-shaped storage unit 30. The modules 141 to 14n are secured to the upper wall of the storage unit 30 that faces each other with the X-ray tube 13, and the amplifier substrates 31 are secured to the lower wall of the storage unit 30. Once a cover has been removed from the front surface 112 of the gantry 11, the amplifier substrates 31 can be slid from and back into the storage unit 30.

Figure 4:
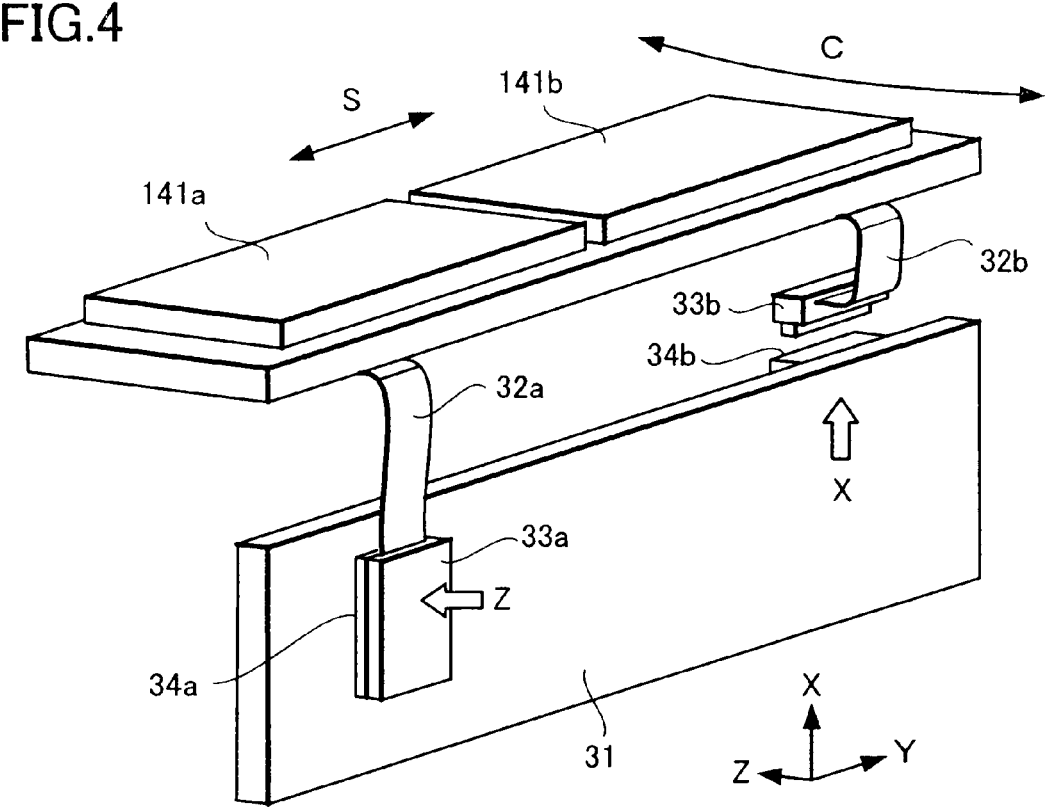
FIG. 4 is a perspective view depicting the major components of the radiation detector according to the embodiment of the invention.

FIG. 4 shows one of module pairs (each composed of a module 141a and a module 141b) and one of the amplifier substrates 31, which is associated with the module pair. FIG. 4 illustrates how the detector modules 141a and 141b of each pair are connected to the associated amplifier substrate 31.

The detector module 141a and the detector module 141b are, for example, 24 mm wide in the channel direction C and 60 to 120 mm long in the slice direction S. The electric signals output from the detector modules 141a and 141b are supplied via flexible flat cable 32a and 32b (hereinafter simply called cables) to connectors 33a and 33b, respectively. The connectors 33a and 33b can be coupled to connectors 34a and 34b provided on the amplifier substrate 31. Note that in FIG. 3, the connectors 33b and 34b are shown, and the connectors 33a and 34a are not shown.

The radiation detector 14 has, in fact, n detector modules 141a, n detector modules 141b and n amplifier substrates 31, which are arranged in the channel direction C. It follows that the radiation detector 14 has n connector groups each consisting of connectors 33a and 33b, and n connector groups each consisting of connectors 34a and 34b.

The cable 32a, connector 33a, connector 34a constitute a coupling unit that electrically connects one detector module 141a to the amplifier substrate 31 associated with the module 141a. Similarly, the cable 32b, connector 33b, connector 34b constitute a coupling unit that electrically connects one detector module 141b to the amplifier substrate 31 associated with the module 141b.

The front side detector module 141a and the amplifier substrate 31 are connected by the connectors 33a and 34a, whereas the back side detector module 141b and the amplifier substrate 31 are connected by the connectors 33b and 34b.

The back side connectors 34b are provided on the upper surfaces of the amplifier substrates 31. Therefore, the connectors 33a and connectors 34b can be pulled out and inserted into only if the amplifier substrates 31 are moved upwards or downwards. The front side connectors 33a can be pulled out from, and inserted into, the connectors 34a provided on the lower surface of the amplifier substrates 31.

In FIG. 4, arrow X indicates the direction in which the amplifier substrates 31 can be moved up and down, arrow Y indicates the direction in which the amplifier substrates 31 can be slid, and arrow Z indicates the direction in which the connectors 33a can be pulled and inserted. As can be understood from FIG. 4, X direction in which the connectors 33a and connectors 34b can be pulled and inserted intersects at right angles with Z direction in which the connectors 33a and connectors 34a can be pulled and inserted.

Figure 5:
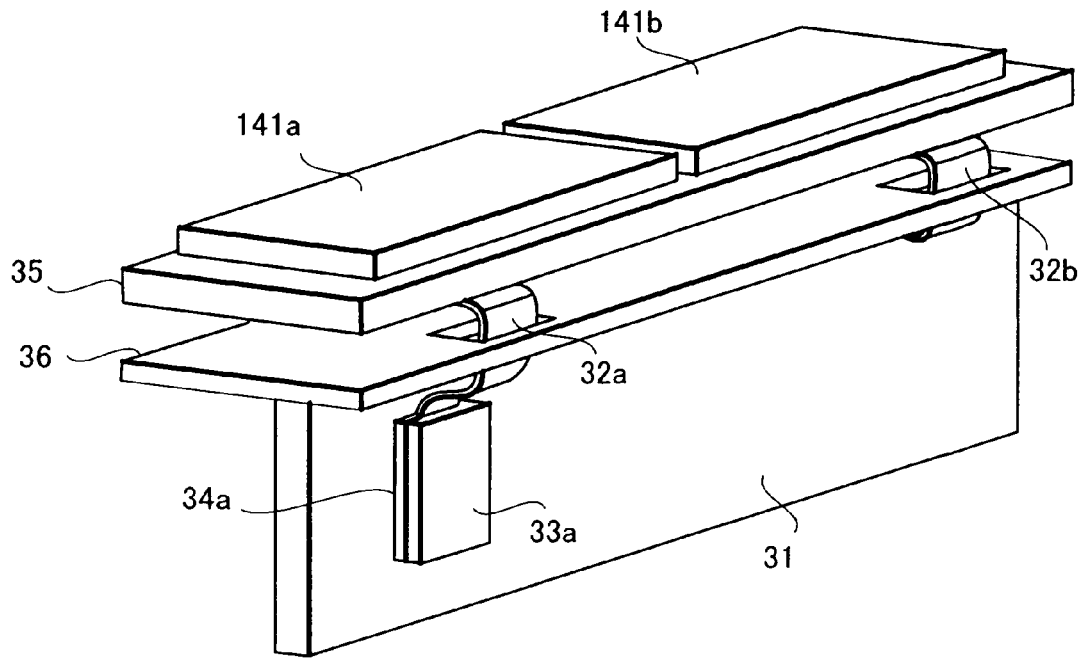
FIG. 5 is another perspective view depicting the major components of the radiation detector according to the embodiment of the invention.

As shown in FIG. 5, an upper plate 35 and a lower plate 36 are used, securing the detector modules 141a, detector modules 141b and amplifier substrates 31 to the storage unit 30.

More specifically, the detector modules 141a and detector modules 141b are attached to the upper plate 35, each with the X-ray detecting face facing upwards as shown in FIG. 5. The cables 32a extend downwards from the detector modules 141a, and the cables 32b extend downwards from the detector modules 141b.

The front side cables 32a extend downwards, passing through the lower plate 36, and are connected to the connectors 33a and 34b. The back side cables 32b are connected to the connectors 33b attached to the bottom of the lower plate through the lower plate 36 (see FIG. 4). The upper plate 35 and lower plate 36 are fastened to the upper wall of the storage unit 30 in FIG. 3. The amplifier substrates 31 can be slid onto the lower wall of the storage unit 30.

The radiation detector 14 according to this invention has a guide unit 40 that can slide and lift up and down the amplifier substrates 31, in order to facilitate the coupling of the back side connectors 33b and the connectors 34b. The guide unit 40 is a coupling mechanism that couples and decouples the connectors 33b to and from the connectors 34b.

FIG. 6A is a front view showing the configuration of the guide unit 40. FIG. 6B and FIG. 6C are side views explaining how the guide unit 40 guides the amplifier substrates 31 into the storage unit 30, thereby to connect the amplifier substrates 31 to the back side connectors 33b and 34b. FIG. 6A shows the guide unit 40 as viewed in Y direction in which the amplifier substrates 31 are inserted into the storage unit 30.

As seen from FIGS. 6A to 6C, holding substrates 41 are fastened to the lower edge of the amplifier substrates 31, respectively. The holding substrates 41 have a guide slit 42 that inclines downwards as it extends deeper in Y direction of the amplifier substrate 31. A plurality of pin members 43 are loosely held in the guide slit 42 of each holding substrate 41.

The pin members 43 pass through the guide slit 42 and secured to a slider 44. The pin members 43 have a head each. The head is larger than the groove width of the guide slit 42, preventing the pin member 43 from slipping out of the guide slit 42.

The sliders 44 are attached to an operation lever 45. The operator can push the operation lever 45 to slide the sliders 44 in Y direction. The slider 44 can slide in Y direction, with its lower edge moving along guide rails 37 and 38 laid on the bottom of the storage unit 30. The holding substrates 41, sliders 44 and operation lever 45 constitute the guide unit 40.

On each amplifier substrate 31, an amplifier circuit is provided to amplify electric signals from two detector modules 141a and 141b. The signals amplified by the amplifier circuit are supplied to the DAS unit 16 through cables (not shown). An analog-to-digital (A/D) converter may be provided on the amplifier substrate 31 in addition to the amplifier circuit, to convert the output of the amplifier circuit to a digital signal.

The connectors 34b are secured to the upper edges of the amplifier substrates 31, respectively. The connectors 33b are secured to the lower plate 36 that faces the connectors 34b. Guide pins 361 protrude from the lower plate 36.

The guide pins 361 work as stoppers and abut on the connectors 34b, respectively, when the amplifier substrates 31 are slid in Y direction.

Each amplifier substrate 31 is fastened to the associated holding substrate 41 with screws 46. Each holding substrate 41 is fastened to the associated slider 44 with the pin members 43. The sliders 44 are attached to the operation lever 45. The amplifier substrates 31, holding substrates 41, sliders 44 and operation lever 45 constitute an integral structure. The integral structure can slide along the guide rails 37 and 38 when the operator pushes the operation lever 45 in Y direction.

More specifically, when the operation lever 45 is pushed in Y direction as shown in FIG. 6B, with the lower edge of the slider 44 inserted in the gap between the guide rails 37 and 38, the amplifier substrates 31, holding substrates 41 and sliders 44 move deeper in the gantry 11. If the operator keeps pushing the operation lever 45, the connectors 34b abut on the guide pins 361.

If the operator further pushes the operation lever 45, with the connectors 34b abutting on the guide pins 361, the slider 44 moves deeper in the gantry 11 as is illustrated in FIG. 6C. At this point, the amplifier substrates 31 and holding substrates 41, which have abutted on the guide pins 361, can no longer move deeper, but the pin members 43 attached to the slider 44 moves still deeper along the guide slit 42. As a result, the holding substrates 41 and the amplifier substrates 31 move upwards (in X direction) along the guide pins 361. The connectors 34b are thereby connected to the connectors 33b.

At this time, the connectors 34b are connected to the connectors 33b, the guide pins 361 hold the connectors 33b and 34b in accurate positions so that poor connection can be prevented. On the other hand, the connectors 33a are connected to the connectors 34a (FIG. 5) by the operator. The operator can easily connect the connectors 33a to the connectors 34a positioned on the front side of the amplifier substrates 31, because these connectors located near the front surface 112 of the gantry 11.

Thus, the connectors 33b and 34b, that lie deep in the storage unit 30, can be coupled easily and accurately by virtue of the guide unit 40. In addition, the connectors 33a and 34a, which lie at the entrance of the storage unit 30, can be easily coupled by the operator.

To pull the amplifier substrates 31 from the storage unit 30, the operator may first disconnect the connectors 34a from the connectors 34b and then pull the operation lever 45. Then, the sliders 44 are pulled in the direction opposite to direction Y (FIG. 6C), and the amplifier substrates 31 and the holding substrates 41 lower along the guide pins 361. The connectors 33b are thereby disconnected from the connectors 34b as shown in FIG. 6B. The amplifier substrates 31 can now be pulled out.

One amplifier substrate 31 can therefore serve for two detector modules 141a and 141b in the present invention. Further, the connectors 33b and 34b arranged at the deeper end of the amplifier substrate 31 can be accurately and easily pulled and inserted. This can enhance the efficiency of manufacture and the efficiency of maintenance work. Furthermore, the cooling efficiency can be raised because the amplifier substrates 31 can be set in vertical position.

The longer the path from the detector modules 141a and 141b to the associated amplifier substrate 31, the more the electrostatic capacitance will increase, inevitably making the circuit noise greater. Nonetheless, the electrostatic capacitance is small and the circuit noise is therefore small in the present invention. This is because the amplifier substrates 31 are arranged along a circular arc and the detector modules 141a are spaced apart from the detector modules 141b by so short a distance as possible, and are connected to the detector modules 141a by flexible flat cables 32a and 32b.

Thus, in the radiation detector according to an embodiment of this invention, two detector modules of each pair share one amplifier substrate. The connectors of these detector modules are therefore simple enough to reduce the possibility of connection error.

The radiation detector according to this invention can be used not only in medical X-ray CT apparatuses, but also in industrial X-ray CT apparatuses configured to inspect products and baggage-inspecting X-ray CT apparatuses for use in airports and similar facilities.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A radiation detector comprising:
a detector block including a plurality of radiation detector modules arranged in a slice direction;
a plurality of cables configured to receive signals from the radiation detector modules of the detector block;
a plurality of connectors associated with the cables, respectively, and spaced, one from another, in the slice direction;
circuit substrates configured to receive signals via the connectors from the radiation detector modules of the detector block;
a storage unit that holds the detector block and the circuit substrates; and
a guide unit that supports the circuit substrates, allowing the circuit substrates to be pulled out from, and inserted into, the storage unit, in the slice direction, and to be moved toward and away from the detector block.

2. The radiation detector according to claim 1, wherein the detector block includes first radiation detector modules arranged in the slice direction and second radiation detector modules arranged in the slice direction, and the connectors are connected to the first radiation detector modules and the second radiation detector modules.

3. The radiation detector according to claim 1, wherein the circuit substrates have an amplifier circuit each, the amplifier circuits being configured to amplify electric signals from the detector modules adjacent in the slice direction.

4. The radiation detector according to claim 1, wherein the guide unit includes sliders integrally secured to the circuit substrates respectively, and the circuit substrates are moved toward the detector modules and are connected to any one of the connectors, when the sliders are moved in the slice direction.

5. The radiation detector according to claim 4, wherein an operation lever is attached to the sliders.

6. The radiation detector according to claim 4, wherein the guide unit has holding substrates secured to the circuit substrates,
each holding substrate has a guide slit inclining to the slice direction and serving to convert the motion of the circuit substrate to motion of a direction intersecting at right angles with the slice direction, and
each slider has pin members loosely fit in the guide slit.

7. The radiation detector according to claim 4, wherein the storage unit contains a stopper that prevents the sliders from being further inserted once the sliders have been inserted into the radiation detector in the slice direction for a predetermined distance.

8. The radiation detector according to claim 7, wherein the stopper comprises guide pins that extend in a direction intersecting at right angles with the slice direction.

9. A radiation detector comprising:
a detector block including a plurality of radiation detector modules arranged in a slice direction;
a plurality of cables configured to receive signals from the radiation detector modules of the detector block;
a plurality of connectors associated with the cables, respectively, and spaced, one from another, in the slice direction; and
circuit substrates configured to receive signals via the connectors from the radiation detector modules of the detector block,
wherein any one of the connectors is provided at that end of one circuit substrate which is distal as viewed in the direction of inserting the circuit substrate, and is moved toward and away from the detector block to be attached to, and detached from, the detector block.

10. An X-ray CT apparatus comprising:
an X-ray tube configured to apply an X-ray beam to an object; and
a radiation detector opposed to the X-ray tube, shaped like a circular arc and configured to detect X-rays passed through the object and convert the X rays into an electric signal, wherein
the radiation detector includes:
a detector block including a plurality of radiation detector modules arranged in a slice direction;
a plurality of cables to receive signals from the radiation detector modules of the detector block;
a plurality of connectors associated with the cables, respectively, and spaced, one from another, in the slice direction;

circuit substrates configured to receive signals via the connectors from the radiation detector modules of the detector block;

a storage unit that holds the detector block and the circuit substrates; and a guide unit that supports the circuit substrates, allowing the circuit substrates to be pulled out from, and inserted into, the storage unit, in the slice direction, and to be moved toward and away from the detector block.

11. An X-ray CT apparatus comprising:

an X-ray tube configured to apply an X-ray beam to an object;

a detector block having a plurality of radiation-detecting element arrays and configured to detect X-rays passed through the object;

circuit substrates configured to process electric signals from the detector block;

first connectors configured to electrically connect the circuit substrates to the detector block;

second connectors spaced apart from the first connectors and configured to electrically connect the circuit substrates to the detector block;

a storage unit that holds the detector block and the circuit substrates; and a guide unit that supports the circuit substrates, allowing the circuit substrates to be pulled out from, and inserted into, the storage unit, in the slice direction, the guide unit configured to couple and decouple connectors provided at the detector block and constituting the first connectors to and from the connectors provided at the circuit substrates.

12. An X-ray CT apparatus comprising:

an X-ray tube configured to apply an X-ray beam to an object;

first detector modules, each including a plurality of radiation-detecting element arrays, and configured to detect X-rays passed through the object;

second detector modules, each including a plurality of radiation-detecting element arrays, and arranged beside the first detector modules with respect to a slice direction;

circuit substrates configured to process electric signals from the first detector modules and second detector modules;

first connectors configured to electrically connect the first detector modules to the circuit substrates; and second connectors configured to electrically connect the second detector modules to the circuit substrates, wherein the first connectors are pulled and inserted in one direction, and the second connectors are pulled and inserted in another direction.

* * * * *